(12) United States Patent
Combe et al.

(10) Patent No.: US 6,197,846 B1
(45) Date of Patent: Mar. 6, 2001

(54) DENTAL ROOT CANAL FILLING, RETROFILLING, AND PERFORATION REPAIR MATERIAL

(75) Inventors: Edward C. Combe, Maplewood; Ernest S. Reeh, Stillwater, both of MN (US)

(73) Assignee: River Valley Endodontics, P.A., Stillwater, MN (US)

( * ) Notice: Subject to any disclaimer, the term of this patent is extended or adjusted under 35 U.S.C. 154(b) by 0 days.

(21) Appl. No.: 09/412,680

(22) Filed: Oct. 5, 1999

Related U.S. Application Data

(62) Division of application No. 09/095,520, filed on Jun. 10, 1998, now Pat. No. 6,028,125.

(51) Int. Cl.$^7$ .............................. A61K 6/083; C08K 3/22; C08K 3/20; C08K 5/09
(52) U.S. Cl. .................... 523/116; 523/117; 523/118; 524/432; 524/433; 524/547; 524/556; 524/832; 524/300
(58) Field of Search .................... 523/116, 117, 523/118; 524/432, 433, 547, 556, 832, 300

(56) References Cited

U.S. PATENT DOCUMENTS

| | | | |
|---|---|---|---|
| 3,028,247 | 4/1962 | Molnar | 106/35 |
| 4,526,544 | 7/1985 | Kahn | 433/224 |
| 4,657,592 | 4/1987 | Takubo | 106/35 |
| 4,806,381 | 2/1989 | Engelbrecht et al. | 523/116 |
| 4,808,228 | 2/1989 | Randklev | 106/35 |
| 4,931,096 | 6/1990 | Fujisawa et al. | 106/35 |
| 5,141,560 | 8/1992 | Combe et al. | 106/35 |
| 5,165,893 | 11/1992 | Thompson | 433/224 |
| 5,236,362 | 8/1993 | Cohen et al. | 433/288.1 |
| 5,263,861 | 11/1993 | Cohen et al. | 433/224 |
| 5,372,759 | 12/1994 | Johnson | 264/16 |
| 5,501,727 | * 3/1996 | Wang et al. | |
| 5,520,922 | * 5/1996 | Gasser et al. | |
| 5,540,766 | 7/1996 | Castellani | 106/35 |
| 5,624,976 | 4/1997 | Klee | 523/116 |
| 5,646,197 | 7/1997 | Martin | 523/116 |
| 5,814,682 | 9/1998 | Rusin et al. | 523/116 |

OTHER PUBLICATIONS

M.P. Goodstein, Pharmaceuticals *Dental Composition*, p. 1962, Apr., 1962.
D.C. Smith, British Dental Journal, *A New Dental Cement*, Nov. 5, 1968, pp. 381–384.
A.D. Wilson et al., British Dental Journal, *A New Translucent Cement for Dentistry*, Feb. 15, 1972, pp. 133–135.
The Science of Endodontics, *Endodontic Materials*, pp. 399–408, 1983.

\* cited by examiner

*Primary Examiner*—Peter A. Szekely
(74) *Attorney, Agent, or Firm*—Kinney & Lange, P.A.

(57) ABSTRACT

The present invention is an endodontic sealer paste and an endodontic core material for root canal filling, retrofilling, and perforation repair. The endodontic sealer paste contains a dry poly(carboxylic acid), zinc oxide, and an aliphatic acid. The endodontic core material contains a pliant polymer, a dry poly(carboxylic acid), and zinc oxide.

20 Claims, No Drawings

DENTAL ROOT CANAL FILLING, RETROFILLING, AND PERFORATION REPAIR MATERIAL

This is application is a division of U.S. application Ser. No. 09/095,520 filed Jun. 10, 1998, now U.S. Pat. No. 6,028,125.

BACKGROUND OF THE INVENTION

The present invention relates generally to root canal filling, retrofilling, and perforation materials. More particularly, the present invention relates to a sealer paste and core material for root canal filling, retrofilling, and perforation.

Endodontic therapy (also identified as root canal therapy) involves the removal of all tooth pulp space contents, potentially infected and diseased tissue and their by-products from the root system of a tooth. Once these materials are removed from the root system, the root canal is shaped to facilitate filling. The root canal is then filled.

While there are many techniques for root canal filling, the most widely used technique uses a combination of gutta percha cones and a zinc oxide-eugenol based sealing material. This technique has also been used with retrograde root canal filings following apicoectomy (also referred to as retrofillings) and for the repair of tooth root perforations.

A critical factor in the long-term success of endodontic therapy involves eliminating leakage around and through a root canal filling, a retrofilling, or a perforation repair. Intimate adaptation of the filling material to the root canal typically plays an important role in eliminating leakage. However, attaining intimate adaptation is difficult.

Johnson, U.S. Pat. No. 5,372,759, and Fujisawa et al., U.S. Pat. No. 4,931,096, describe using warm vertical condensation of gutta percha to reduce leakage around and through the root canal filling. Takubo, U.S. Pat. No. 4,657,592, describes using a filling material that remains semi-solid at body temperature but which is softened by heating during the filling process.

One variation in endodontic sealers is to replace the aromatic compound eugenol with carboxylic acids that react with zinc oxide. For example, Molnar, U.S. Pat. No. 3,028,247 describes using caprylic acid (also known as octanoic acid) and lauric acid (also known as dodecanoic acid) as reactants.

Dainippon Toryo KK, Japanese Patent No. 3,027,309, describes using a sealer that adheres to the gutta percha cone to reduce leakage through the root canal filling material. However, potential problems that are associated with leakage at the margins with dentin are still experienced.

Kahn, U.S. Pat. No. 4,526,544, discusses using cyanoacrylate adhesives to bond both to dentin and gutta percha. A drawback of the cyanoacrylate adhesives is that they chemically break down in biological environments, such as are present in the mouth.

In an article entitled, A New Dental Cement, 125 British Dental J. 381 (1968), Smith describes mixing an aqueous solution of poly(acrylic acid) with zinc oxide. This adhesive was identified as zinc polycarboxylate or zinc polyacrylate cement.

It has also been described to use poly(acrylic acid) or a closely related co-polymer with aluminosilicate glass powders to produce translucent dental cement. Wilson et al., 132 British Dental J. 133 (1972). Wilson et al. indicates that the polymer is either in aqueous solution or a dry powder, which is mixed with water.

Combe et al., U.S. Pat. No. 5,141,560, discloses a calcium hydroxide pulp-capping material that is prepared from a non-aqueous cement that contains dry poly(acrylic acid). Adhesion to dentin was achieved through moisture from the tooth structure being absorbed into the cement. This absorption results in partial dissolution of the polymer.

The prior art root canal obturation materials generally fall into three general groups. The first group is gutta percha cone with zinc oxide-euaenol paste. The second group is glass ionomer. The third group is calcium hydroxide.

These root canal filing materials each typically exhibit good dimensional stability, are radiopaque, and do not provoke an immune response. These materials are also bacteriostatic, sterilizable, non-mutagenic, and non-carcinogenic.

Several drawbacks of the gutta percha cone and zinc oxide-eugenol paste technique are that these materials do not form a hermetic seal. The gutta percha/zinc oxide-eugenol material also tends to irritate periapical tissues and is porous to moisture. Additionally, the gutta percha/zinc oxide-eugenol material is degraded by long-term exposure to tissue fluids that are typically present in the mouth.

It is difficult to form a hermetic seal of the root canal using glass ionomer. Glass ionomer is not impervious to moisture and is not non-porous. Another drawback of glass ionomer is that it is difficult to remove the glass ionomer when it is necessary to retreat the root canal. Yet another drawback of glass ionomer is that glass ionomer irritates periapical tissue.

The calcium hydroxide technique has a very limited working time before setting. It is also difficult to form a hermetic seal with the calcium hydroxide filling material. The calcium hydroxide filling material is degraded by long-term exposure to tissue fluids that are typically present in the mouth. This material is also not impervious to moisture.

BRIEF SUMMARY OF THE INVENTION

The present invention is an endodontic sealer paste that contains: (a) a dry poly(carboxylic acid), a precursor transformable into the dry poly(carboxylic acid), or a dry cation-crosslinkable polymeric acid containing on average one phosphonic acid group per one to three backbone carbon atoms; (b) zinc oxide, magnesium oxide, calcium oxide, zinc hydroxide, magnesium hydroxide, calcium hydroxide, hydroxyapatite, or a combination thereof; and (c) an aliphatic acid in the series $CH_3(CH_2)_nCOOH$, a branched chain aliphatic acid, a fatty acid triglyceride, an aromatic compound capable of reacting (b), or a combination thereof.

The present invention also includes an endodontic core material that contains (a) a pliant polymer, (b) a dry poly(carboxylic acid), a precursor transformable into the dry poly(carboxylic acid), or a dry cation-crosslinkable polymeric acid containing on average one phosphonic acid group per one to three backbone carbon atoms; and (c) zinc oxide, magnesium oxide, calcium oxide, zinc hydroxide, magnesium hydroxide, calcium hydroxide, hydroxyapatite, or a combination thereof.

DETAILED DESCRIPTION

The present invention is a sealer paste and a core material for use in conjunction with root canal filling, retrofilling, and perforation repair. When the core material and the sealer paste of the present invention are used in endodontic obturation, there is an adhesive continuum that is attained through commonality of adhesive constituents between the sealer paste and the core material. Therefore, an impervious bond is formed between the sealer paste and the dentin and between the sealer paste and the core material. The adhesion between the elements is continually replenished because the sealer paste and the core material are non-aqueous and because there is an excess concentration of poly(carboxylic acid) in the sealer paste and the core material.

Because of these characteristics, the sealer paste and the core material prevent or significantly reduce apical leakage when produced and used according to the present invention. By preventing or significantly reducing apical leakage, the sealer paste and core material of the present invention significantly enhance the long-term success rate of the root canal filling, retrofilling, or perforation repair.

Further advantages of the sealer paste and the core material of the present invention are that these materials do not shrink or change form after insertion into the root canal. The materials also provide ample time for working before setting. Additionally, the materials do not provoke an immune response, are non-mutagenic, and non-carcinogenic. The present invention is also bacteriostatic, sterilizable, radiopaque, impervious to moisture, and non-porous. The sealer paste and the core material are removable when it is desired to retreat the root canal.

The sealer paste preferably contains poly(carboxylic acid), zinc oxide, and an aliphatic acid. The sealer paste also preferably includes a radiopaque material, viscosity and consistency modifiers, and biologically active agents. The poly(carboxylic acid) provides adhesion to dentin and to the core material. The zinc oxide reacts with the poly(carboxylic acid) and the aliphatic acids and also contributes to the radiopacity. The aliphatic acids react with zinc oxide to give a setting reaction and provide a carrier for the paste.

Preferred poly(carboxylic acid)s are prepared by the homopolymerisation and copolymerisation of unsaturated aliphatic carboxylic acids for example aconitic acid, acrylic acid, citraconic acid, fumaric acid, glutaconic acid, itaconic acid, maleic acid, mesaconic acid, methacrylic acid, 3-butene 1,2,3 tricarboxylic acid and tiglic acid; and the copolymerisation of these acids with other unsaturated aliphatic monomers for example vinyl monomers, such as vinyl hydrocarbon monomers, vinyl ethers, acrylamide or acrylonitrile. Particularly preferred are the homopolymers of acrylic acid and its copolymers with one or more of aconitic, fumaric, itaconic, maleic, mesaconic, methacrylic, muconic or tiglic acid, particularly copolymers of acrylic acid and itaconic acid. Especially preferred are homopolymers of acrylic acid. Good results are also possible using copolymers of vinyl methyl ether and maleic acid.

The term poly(carboxylic acid), as used herein, also encompasses precursors of poly(carboxylic acid) and cation crosslinkable polymeric acid containing on average one phosphonic acid group per one or more backbone carbon atoms. Poly(acrylic acid) may be prepared by hydrolysis of corresponding polyacrylonitriles. The precursor of a poly (carboxylic acid) may be a homopolymer of an unsaturated carboxylic acid anhydride or a copolymer with another carboxylic acid or anhydride thereof. The precursor of a poly(carboxylic acid) may also be a copolymer of an unsaturated carboxylic acid anhydride with an unsaturated aliphatic monomer, for example vinyl monomers, such as vinyl hydrocarbon monomers, vinyl ethers, acrylamide or acrylonitrile. Good results may be obtained by using homopolymers of maleic anhydride or vinyl orthophthalic anhydride, or copolymers thereof, especially block copolymers thereof, with ethylene, propylene, butenes, styrene and vinyl methyl ether.

The poly(carboxylic acid) or precursor thereof is preferably linear, although branched polymers may also be used. Preferably, the poly(carboxylic acid) has an average molecular weight of between about 10,000 and 4,000,000.

The poly(carboxylic acid) is used at a stoichiometric excess concentration in the sealer paste so that a portion of the poly(carboxylic acid) remains unreacted in the sealer paste. A portion of the poly(carboxylic acid) is able to remain unreacted in the sealer paste because the sealer paste is non-aqueous. The unreacted poly(carboxylic acid) is available to slowly react in situ to enhance long-term adhesion between the components and thereby hinder microleakage. The concentration of the poly(carboxylic acid) in the sealer paste is preferably between about 5 and 20 percent by weight. Unless indicated otherwise, all references to percent concentration are percent by weight.

In addition to or in substitute of zinc oxide, oxides or hydroxides of zinc, calcium and magnesium may also be used in formulating the sealer paste of the present invention. Preferred alternatives include magnesium oxide, calcium oxide, zinc hydroxide, magnesium hydroxide, calcium hydroxide, hydroxyapatite, or a combination thereof. The concentration of the zinc oxide and alternatives in the sealer paste is preferably between about 10 and 50 percent.

Preferred aliphatic acids for use in the present invention include octanoic acid, dodecanoic acid, heptanoic acid, tridecanoic acid, or combinations thereof. The aliphatic acids are used in the sealer paste at a concentration of up to 50 percent. Some or all of the aliphatic acids may be replaced with aromatic reactants that have a concentration of up to 40 percent. Preferred aromatic reactants for use with the present invention include eugenol, 2-ethoxybenzoic acid, or combinations thereof.

The radiopaque material is preferably a salt or oxide of silver (e.g. silver iodide), barium (e.g. barium sulfate), or bismuth (e.g. bismuth carbonate, bismuth subcarbonate, or bismuth trioxide). The radiopaque material may also be a metal (e.g. tungsten, silver, titanium, or tantalum), glass frits containing heavy metals (e.g. barium or bismuth), or organo-iodine compounds. The concentration of the radiopaque material in the sealer paste is up to about 60 percent.

The viscosity, consistency modifiers and agents to prevent component separation preferably include solids, such as hydrogenated rosin and partially hydrogenated rosin, and liquids, such as mineral oil. Fatty acids may also be used to modify the viscosity and consistency of the sealer paste. Additionally trans-1,4-polyisoprene can be included in the sealer to enhance commonality of components between the sealer and the core or as a viscosity modifier. The concentration of the viscosity and consistency modifiers in the sealer paste is up to 50 percent.

The biologically active agents include antimicrobials, antibiotics and steroids. A preferred biologically active agent for use in the present invention is benzoic acid. The AgI of the radiopacifiers also has anti-microbial properties and thus serves a dual function. The concentration of the biologically active agents, not including AgI is up to 30 percent.

The sealer paste is preferably fabricated in two parts that are mixed together when it is desired to use the sealer paste. Fabricating the paste sealer in a two-part format provides the paste sealer with a long shelf life. When the two parts are mixed together, the sealer paste does not set for over an hour when stored at an ambient temperature of approximately 21° C. However, the sealer paste readily sets in approximately 30–45 minutes when applied in the root canal opening, which was at a temperature of approximately 37° C. and 100 percent relative humidity and can be modified to provide shorter setting times. The first part preferably contains poly(carboxylic acid), aliphatic acid, consistency modifier, and preservative. The second part preferably contains zinc oxide, radiopaque material, and consistency modifier.

The core material preferably contains poly(carboxylic acid), zinc oxide, and a pliant polymer. The core material may also contain a radiopaque material, a plasticizer, biologically active agents, and a coloring agent. The poly(carboxylic acid) facilitates bonding with the sealer paste. The zinc oxide reacts with acids in the sealer paste and contributes to the radiopacity. The pliant polymer provides a polymer matrix that acts as a vehicle for other constituents.

The poly(carboxylic acid) used in the core material is selected based on the criteria set forth above for selecting the poly(carboxylic acid) for the sealer paste. The poly(carboxylic acid) is used at a stoichiometric excess concentration in the core material so that a portion of the poly(carboxylic acid) remains unreacted in the core material. A portion of the poly(carboxylic acid) is able to remain unreacted in the core material because the core material is non-aqueous. The unreacted poly(carboxylic acid) is available to slowly react in situ to enhance long-term adhesion between the components and thereby hinder microleakage. The concentration of the poly(carboxylic acid) in the core material is between about 2 and 20 percent.

Oxides or hydroxides of zinc, calcium and magnesium may be used in addition to or in substitute of zinc oxide in formulating the core material of the present invention. The concentration of the zinc oxide and alternatives in the core material is preferably between about 10 and 50 percent.

The pliant polymer is preferably gutta percha. As obtained naturally, gutta percha comprises the purified exudate of various trees of the genus Palagunium, Sapotaceae. A synthetic form of gutta percha is trans-1,4-polyisoprene. Advantages of gutta percha is that it improves pliability, compressibility and low permeability of a dental composition. Additionally, gutta percha is inert to dental and periapical tissue. A person of ordinary skill in the art will appreciate that it is also possible to use other synthetic or naturally occurring pliant materials that exhibit similar characteristics, such as balata. The concentration of the pliant polymer in the core material is between about 10 and 30 percent.

The radiopaque materials set forth with respect to the sealer paste are also suitable for use in the core material. The concentration of the radiopaque material in the core material is up to about 40 percent.

Preferred plasticizers for use in the core material are ethyl stearate or di-n-butyl phthalate. A person of ordinary skill in the art will appreciate that it is possible to select other plasticizers when formulating the core material of the present invention. The concentration of plasticizer in the core material is preferably up to about 10 percent.

The biologically active agents set forth with respect to the sealer paste are also suitable for use in the core material. The concentration of the biologically active agents in the core material is up to 20 percent.

Coloring agents are incorporated into the core material to provide the core material with a contrasting color to the color of the tooth so that the core material is identifiable. A preferred coloring agent for use in the present invention is tartazine. The concentration of the coloring agent in the core material is up to 10 percent by weight.

In use, an opening that exposes the root canal is prepared and the canal is cleaned and shaped using conventionally known endodontic techniques. The first and second components of the sealer paste are mixed together in approximately equal amounts by weight until the sealer paste is substantially homogeneous. The sealer paste is then applied to the walls of the canal until the surfaces of the walls are substantially covered. An outer surface of the core material is preferably covered with the sealer paste. The core material is inserted into the opening and then urged into intimate contact with the opening. The process is repeated using additional core materials until the canal is filled.

The performance of the root canal filling, retrofilling, and perforation repair materials was analyzed in performing the following examples. The examples are intended to exhibit the characteristics of the materials according to the present invention and are not intended to limit the scope of the invention.

EXAMPLE 1

A core material was prepared with the following materials and concentrations: zinc oxide (50 percent by weight), gutta percha (20 percent by weight), silver iodide (15 percent by weight), poly(acrylic acid) having an average molecular weight of about 3,000,000 (10 percent by weight), ethyl stearate (3.5 percent by weight), and tartazine (1.5 percent by weight). The materials were mixed together and then shaped into root canal filling cones using conventionally known techniques.

The sealer paste was prepared in a two-part form. Part one of the sealer paste contained octanoic acid (10 percent by weight), dodecanoic acid (30 percent by weight), partially hydrogenated rosin (30 percent by weight), and poly(acrylic acid) having an average molecular weight of about 450,000 (30 percent by weight). Part two of the sealer paste contained silver iodide (50 percent by weight), zinc oxide (30 percent by weight), partially hydrogenated rosin (10 percent by weight), and mineral oil (10 percent by weight)

Part one and part two of the sealer paste were mixed together in approximately equal weight proportions to prepare the sealer paste. The sealer paste had an acceptable viscosity that permitted the sealer paste to be readily applied in the root canal. The sealer paste did not exhibit setting for more than one hour when stored at an ambient temperature of approximately 21° C. However, the sealer paste readily sets in about 30–45 minutes when applied in the root canal opening, which was at a temperature of approximately 37° C. and 100 percent relative humidity.

The performance of the sealer paste and the core material of the present invention were compared to the performance of a conventional gutta percha cone and zinc oxide-eugenol sealer (hereinafter "the control").

The performance of the sealer paste and the core material was evaluated based upon the microleakage exhibited in a root canal filling. Ten samples of each material were evaluated for each material and the mean microleakage as well as the standard deviation are reported in Table 1.

TABLE 1

| Mean Microleakage | |
| --- | --- |
| Present Invention | 0.49 ± 0.27 millimeters |
| Control | 3.75 ± 2.81 millimeters |

The results indicate that the mean microleakage for the present invention were nearly a factor of 10 lower than the mean microleakage exhibited by the control. These results indicate that the sealer paste and the core material of the present invention exhibit a greater amount of adhesion than adhesion exhibited by the control. The smaller amount of microleakage exhibited by the sealer paste and the core material of the present invention indicate that there is a greater likelihood of the long term success of the root canal using the sealer paste and the core material of the present invention when compared with the long-term performance of the control.

EXAMPLE 2

A core material was prepared with the following materials and concentrations: zinc oxide (40 percent by weight), gutta percha (20 percent by weight), barium sulfate (25 percent by weight), poly(acrylic acid) having an average molecular weight of about 1,250,000 (10 percent by weight), and dibutyl phthalate (5 percent by weight). The materials were mixed together and then shaped into root canal filling cones using conventionally known techniques.

The sealer paste was prepared in a two-part form. Part one of the sealer paste contained heptanoic acid (10 percent by weight), tridecanoic acid (30 percent by weight), partially hydrogenated rosin (30 percent by weight), and poly(acrylic acid) having an average molecular weight of about 750,000 (30 percent by weight). Part two of the sealer paste contained barium sulfate (60 percent by weight), zinc oxide (20 percent by weight), partially hydrogenated rosin (10 percent by weight), and mineral oil (10 percent by weight).

Part one and part two of the sealer paste were mixed together in approximately equal weight proportions to prepare the sealer paste. The sealer paste had an acceptable viscosity that permitted the sealer paste to be readily applied in the root canal. The sealer paste did not exhibit setting for more than one hour when stored at an ambient temperature of approximately 21° C. However, the sealer paste readily sets in about 30–45 minutes when applied in the root canal opening, which was at a temperature of approximately 37° C. and 100 percent relative humidity.

The sealer paste was applied to the root canal walls so that the sealer paste substantially covered the surface. Sealer paste was applied to the core material and the core material was urged into the opening using conventionally known techniques.

After the sealer paste was given sufficient time to cure, the adhesion between the dentin, the sealer paste, and the core material was examined. It was found that a bond existed between the sealer paste and the dentin as well as between the sealer paste and the core material. However, it was possible to remove the core material from the root canal, such as would be required to retreat the root canal.

EXAMPLE 3

A core material was prepared with the following materials and concentrations: zinc oxide (40 percent by weight), gutta percha (25 percent by weight), bismuth subcarbonate (20 percent by weight) poly(acrylic acid) having an average molecular weight of about 750,000 (10 percent by weight), and long chain hydrocarbon wax (5 percent by weight). The materials were mixed together and then shaped into root canal filling cones using conventionally known techniques.

The sealer paste was prepared in a two-part form. Part one of the sealer paste contained octanoic acid (10 percent by weight), dodecanoic acid (30 percent by weight), partially hydrogenated rosin (20 percent by weight), ethyl stearate (10 percent by weight), and poly(acrylic acid) having an average molecular weight of about 450,000 (30 percent by weight). Part two of the sealer paste contained powdered silver (50 percent by weight), zinc oxide (30 percent by weight), partially hydrogenated rosin (10 percent by weight), and mineral oil (10 percent by weight)

Part one and part two of the sealer paste were mixed together in approximately equal weight proportions to prepare the sealer paste. The sealer paste had an acceptable viscosity that permitted the sealer paste to be readily applied in the root canal opening. The sealer paste did not exhibit setting for more than one hour when stored at an ambient temperature of approximately 21° C. However, the sealer paste readily sets in about 30–45 minutes when applied in the root canal opening, which was at a temperature of approximately 37° C. and 100 percent relative humidity.

The sealer paste was applied to a root canal walls so that the sealer paste substantially covered the surface. Sealer paste was applied to the core material and the core material was urged into the opening using conventionally known techniques.

After the sealer paste was given sufficient time to cure, the adhesion between the dentin, the sealer paste, and the core material was examined. It was found that a bond existed between the sealer paste and the dentin as well as between the sealer paste and the core material. However, it was possible to remove the core material from the root canal, such as would be required to retreat the root canal.

EXAMPLE 4

The performance of the sealer paste and the core material of the present invention were evaluated for retrofilling using the same material prepared in Example 1. This was compared with commercially available formulations of dental amalgam, Super EBA (a reinforced Zinc Oxide-ethoybenzoic acid/eugenol cement from Harry J. Bosworth Company of Skokie, Ill.), and mineral trioxide aggregate.

The leakage scores measured the maximum leakage from the end of the retrofilling preparation. The results of the study are reported in Table 2. The designations used for characterizing the microleakage are as follows: None (0–0.49 millimeters), slight (0.50–0.99 millimeters), intermediate (1.00–1.49 millimeters), moderate (1.50–1.99 millimeters), extensive (2.00 to end of retrofill, but not around the floor), and through and through (around floor of retrofill and/or into remaining canal).

TABLE 2

| | Frequency of Observation | | | | | |
|---|---|---|---|---|---|---|
| | None | Slight | Intermediate | Moderate | Extensive | Through and through |
| Dental Amalgam | 0 | 0 | 0 | 1 | 6 | 3 |
| Super EBA | 0 | 0 | 0 | 2 | 0 | 8 |
| Mineral Trioxide Aggregate* | 0 | 0 | 0 | 0 | 0 | 10 |
| Present Invention | 0 | 3 | 2 | 3 | 2 | 0 |

*Exposed to dye immediately upon placement in tooth and not allowed to set.

The sealer paste and the core material of the present invention demonstrated a statistically significant lower leakage (p=0.05) than the other materials examined in this study. These results indicate that the results obtained by the sealer paste and core material of the present invention would tend to produce an enhanced long-term prognosis of a successful root canal filling, retrofilling, or perforation repair when compared to the prior art techniques.

Although the present invention has been described with reference to preferred embodiments, workers skilled in the art will recognize that changes may be made in form and detail without departing from the spirit and scope of the invention.

What is claimed is:

1. An endodontic sealer paste comprising a non-aqueous mixture of:
    (a) a dry poly(carboxylic acid), a precursor transformable into the dry poly(carboxylic acid), or a dry cation-crosslinkable polymeric acid containing on average one phosphonic acid group per one to three backbone carbon atoms;
    (b) zinc oxide, magnesium oxide, calcium oxide, zinc hydroxide, magnesium hydroxide, calcium hydroxide, hydroxyapatite, or a combination thereof; and
    (c) an aliphatic acid in the series $CH_3(CH_2)_nCOOH$, a branched chain aliphatic acid, a fatty acid triglyceride, or a combination thereof.

2. The endodontic sealer paste of claim 1 wherein the concentration of (a) in the endodontic sealer paste is between about 2 and 20 percent by weight.

3. The endodontic sealer paste of claim 1 wherein the concentration of (b) in the endodontic sealer paste is between about 10 and 50 percent by weight.

4. The endodontic sealer paste of claim 1 wherein the concentration of (c) in the endodontic sealer paste is about 50 percent or less by weight.

5. The endodontic sealer paste of claim 1 wherein the aromatic compound in (c) is eugenol, 2-ethoxybenzoic acid, or combinations thereof.

6. The endodontic sealer paste of claim 1, and further comprising a radiopaque material.

7. The endodontic sealer paste of claim 6 wherein the concentration of the radiopaque material in the endodontic sealer paste is about 60 percent or less by weight.

8. The endodontic sealer paste of claim 6 wherein the radiopaque material is a salt or oxide of silver, barium, or bismuth; a metal; glass frits containing heavy metals; an organo-iodine compound, or a combination thereof.

9. The endodontic sealer paste of claim 1, and further comprising a viscosity modifier.

10. The endodontic sealer paste of claim 9 wherein the concentration of the viscosity modifier in the endodontic sealer paste is about 50 percent or less by weight.

11. The endodontic sealer paste of claim 9 wherein the viscosity modifier is hydrogenated rosin, partially hydrogenated rosin, mineral oil, fatty acids, trans-1,4-polyisoprene, or combinations thereof.

12. The endodontic sealer paste of claim 1, and further comprising a preservative, an antimicrobial agent, an antibiotic, a steroid, or a combination thereof.

13. The endodontic sealer paste of claim 12 wherein the concentration of the preservative, the antimicrobial agent, the antibiotic, the steroid, or the combination thereof in the endodontic sealer paste is about 20 percent or less by weight.

14. An endodontic filling prepared using the endodontic sealer paste of claim 1.

15. An endodontic perforation repair prepared using an endodontic core material comprising:
    (a) a dry poly(carboxylic acid), a precursor transformable into the dry poly(carboxylic acid), or a dry cation-crosslinkable polymeric acid containing on average one phosphonic acid group per one to three backbone carbon atoms;
    (b) zinc oxide, magnesium oxide, calcium oxide, zinc hydroxide, magnesium hydroxide, calcium hydroxide, hydroxyapatite, or a combination thereof; and
    (c) a pliant polymer.

16. An endodontic kit for root canal filling, retrofilling, and perforation repair, the endodontic kit comprising:
    a sealer paste comprising a mixture of:
        a dry poly(carboxylic acid), a precursor transformable into the dry poly(carboxylic acid), or a dry cation-crosslinkable polymeric acid containing on average one phosphonic acid group per one to three backbone carbon atoms;
        zinc oxide, magnesium oxide, calcium oxide, zinc hydroxide, magnesium hydroxide, calcium hydroxide, hydroxyapatite, or a combination thereof; and
        an aliphatic acid in the series $CH_3(CH_2)_nCOOH$, a branched chain aliphatic acid, a fatty acid triglyceride, an aromatic compound capable of reacting with (b), or a combination thereof; and
    a core material comprising a mixture of:
        a dry poly(carboxylic acid), a precursor transformable into the dry poly(carboxylic acid), or a dry cation-crosslinkable polymeric acid containing on average one phosphonic acid group per one to three backbone carbon atoms;
        zinc oxide, magnesium oxide, calcium oxide, zinc hydroxide, magnesium hydroxide, calcium hydroxide, hydroxyapatite, or a combination thereof; and
        a pliant polymer.

17. A method of treating a root canal, the method comprising:
    forming an opening in a tooth that exposes a root canal of the tooth, wherein the opening has a surface;
    preparing a sealer paste by mixing together:
        a dry poly(carboxylic acid), a precursor transformable into the dry poly(carboxylic acid), or a dry cation-crosslinkable polymeric acid containing on average one phosphonic acid group per one to three backbone carbon atoms;
        zinc oxide, magnesium oxide, calcium oxide, zinc hydroxide, magnesium hydroxide, calcium hydroxide, hydroxyapatite, or a combination thereof; and
        an aliphatic acid in the series $CH_3(CH_2)_nCOOH$, a branched chain aliphatic acid, a fatty acid triglyceride, an aromatic compound capable of reacting with (b), or a combination thereof;
    preparing a core material by mixing together:
        a dry poly(carboxylic acid), a precursor transformable into the dry poly(carboxylic acid), or a dry cation-crosslinkable polymeric acid containing on average one phosphonic acid group per one to three backbone carbon atoms;
        zinc oxide, magnesium oxide, calcium oxide, zinc hydroxide, magnesium hydroxide, calcium hydroxide, hydroxyapatite, or a combination thereof; and
        a pliant polymer;
    applying the sealer paste to the surface in the opening; and
    inserting the core material into the opening so that the core material substantially fills the opening.

18. The method of claim 17 wherein preparing the sealer paste comprises:

forming a first paste portion comprising a mixture of:
  a dry poly(carboxylic acid), a precursor transformable into the dry poly(carboxylic acid), or a dry cation-crosslinkable polymeric acid containing on average one phosphonic acid group per one to three backbone carbon atoms;
  an aliphatic acid in the series $CH_3(CH_2)_nCOOH$, a branched chain aliphatic acid, a fatty acid triglyceride, an aromatic compound capable of reacting with (b), or a combination thereof; and
  a first viscosity modifier;
forming a second paste portion comprising a mixture of:
  zinc oxide, magnesium oxide, calcium oxide, zinc hydroxide, magnesium hydroxide, calcium hydroxide, hydroxyapatite, or a combination thereof; and
  a second viscosity modifier; and
mixing the first paste portion and the second paste portion together to produce the sealer paste.

19. The method of claim 17 wherein the sealer paste does not exhibit setting for at least one hour when stored at an ambient temperature of approximately 21° C.

20. The endodontic perforation repair of claim 15 and further comprising an endodontic sealer paste, the endodontic sealer paste comprising a non-aqueous mixture of:
  (a) a dry poly(carboxylic acid), a precursor transformable into the dry poly(carboxylic acid), or a dry cation-crosslinkable polymeric acid containing on average one phosphonic acid group per one to three backbone carbon atoms;
  (b) zinc oxide, magnesium oxide, calcium oxide, zinc hydroxide, magnesium hydroxide, calcium hydroxide, hydroxyapatite, or a combination thereof; and
  (c) an aliphatic acid in the series $CH_3(CH_2)_nCOOH$, a branched chain aliphatic acid, a fatty acid triglyceride, an aromatic compound capable of reacting with (b), or a combination thereof.

* * * * *